United States Patent
Richards et al.

(10) Patent No.: US 10,517,783 B2
(45) Date of Patent: Dec. 31, 2019

(54) THERAPY ENABLER TOKEN

(71) Applicant: Hill-Rom Services, Inc., Batesville, IN (US)

(72) Inventors: Sandy M. Richards, Pershing, IN (US); Stephen L. Douglas, Batesville, IN (US); Ruchik A. Amin, Batesville, IN (US); Timothy J. Receveur, Guilford, IN (US); Irvin J. Vanderpohl, III, Greensburg, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 801 days.

(21) Appl. No.: 15/243,015

(22) Filed: Aug. 22, 2016

(65) Prior Publication Data

US 2016/0354264 A1    Dec. 8, 2016

Related U.S. Application Data

(63) Continuation of application No. 14/253,897, filed on Apr. 16, 2014, now Pat. No. 9,427,365, which is a
(Continued)

(51) Int. Cl.
*A61G 7/00*   (2006.01)
*A61G 7/05*   (2006.01)
*A61G 7/018*  (2006.01)
*A61G 7/057*  (2006.01)
*A61G 7/015*  (2006.01)
(Continued)

(52) U.S. Cl.
CPC .............. *A61G 7/05* (2013.01); *A61G 7/015* (2013.01); *A61G 7/018* (2013.01); *A61G 7/0506* (2013.01); *A61G 7/0507* (2013.01); *A61G 7/0573* (2013.01); *A61G 7/05769* (2013.01); *A61G 7/05776* (2013.01); *A61H 1/003* (2013.01); *A61H 9/0078* (2013.01); *A61H 23/00* (2013.01); *A61H 23/006* (2013.01); *A61G 2203/12* (2013.01); *A61G 2205/60* (2013.01); *A61H 2201/0146* (2013.01); *A61H 2201/0184* (2013.01); *A61H 2201/502* (2013.01);
(Continued)

(58) Field of Classification Search
CPC ........................................................ A61G 7/00
USPC ...................... 5/600, 616, 613–615, 713–715
See application file for complete search history.

(56) References Cited

U.S. PATENT DOCUMENTS 5,561,412 A   10/1996  Novak et al.
5,699,038 A   12/1997  Ulrich et al.
(Continued)

OTHER PUBLICATIONS

What is an iButton?—Maxim, http://www.maxim-ic.com/products/ibutton/ibuttons/, printed out Oct. 14, 2011, 2 pages.

*Primary Examiner* — Fredrick C Conley
(74) *Attorney, Agent, or Firm* — Barnes & Thornburg LLP

(57) ABSTRACT

A patient support apparatus includes a patient support structure, such as a bed frame or mattress or both, that is configured to support a patient in a recumbent position. The patient support structure is configured to provide at least one therapy to a patient. A therapy enabler token is coupleable to the patient support structure. The at least one therapy is disabled when the therapy enabler token is decoupled from the patient support structure and the at least one therapy is enabled in response to the therapy enabler token being coupled to the patient support structure.

33 Claims, 12 Drawing Sheets

Related U.S. Application Data continuation of application No. 13/281,474, filed on Oct. 26, 2011, now Pat. No. 8,707,483.

(51) Int. Cl.
- *A61H 9/00* (2006.01)
- *A61H 23/00* (2006.01)
- *A61H 1/00* (2006.01)

(52) U.S. Cl.
CPC ............... *A61H 2201/5012* (2013.01); *A61H 2201/5097* (2013.01)

(56) References Cited

U.S. PATENT DOCUMENTS

| | | | |
|---|---|---|---|
| 5,838,223 A | 11/1998 | Gallant et al. | |
| 6,047,424 A | 4/2000 | Osborne et al. | |
| 6,119,291 A | 9/2000 | Osborne et al. | |
| 6,147,592 A | 11/2000 | Ulrich et al. | |
| 6,362,725 B1 | 3/2002 | Ulrich et al. | |
| 6,897,780 B2 | 5/2005 | Ulrich et al. | |
| 7,242,308 B2 | 7/2007 | Ulrich et al. | |
| 7,319,386 B2 | 1/2008 | Collins, Jr. et al. | |
| 7,443,302 B2 | 10/2008 | Reeder et al. | |
| 7,538,659 B2 | 5/2009 | Ulrich et al. | |
| 7,641,623 B2 | 1/2010 | Biondo et al. | |
| 7,746,218 B2 | 6/2010 | Collins, Jr. et al. | |
| 7,849,545 B2 | 12/2010 | Flocard et al. | |
| 8,026,821 B2 | 9/2011 | Reeder et al. | |
| 8,052,626 B2 | 11/2011 | Huster et al. | |
| 8,214,566 B2 | 7/2012 | Edwards et al. | |
| 8,333,317 B2 | 12/2012 | Buer et al. | |
| 8,344,848 B2 | 1/2013 | Möschl et al. | |
| 8,707,483 B2 | 4/2014 | Richards et al. | |
| 9,427,365 B2 | 8/2016 | Richards et al. | |
| 2006/0258964 A1 | 11/2006 | Biondo et al. | |
| 2007/0273517 A1 | 11/2007 | Govind | |
| 2008/0021355 A1* | 1/2008 | Huster | A61H 9/0078 601/149 |
| 2009/0212925 A1 | 8/2009 | Schuman, Sr. et al. | |
| 2009/0212956 A1 | 8/2009 | Schuman et al. | |
| 2009/0214009 A1 | 8/2009 | Schuman, Sr. et al. | |
| 2009/0217080 A1 | 8/2009 | Ferguson et al. | |
| 2011/0247139 A1 | 10/2011 | Tallent et al. | |
| 2012/0110741 A1 | 5/2012 | Mears et al. | |
| 2013/0104906 A1 | 5/2013 | Richards et al. | |
| 2014/0228719 A1 | 8/2014 | Richards et al. | |

\* cited by examiner

THERAPY ENABLER TOKEN

CROSS REFERENCE TO RELATED APPLICATIONS

This application which is a continuation of U.S. application Ser. No. 14/253,897, filed Apr. 16, 2014, to be issued as U.S. Pat. No. 9,427,365, which is a continuation of U.S. application Ser. No. 13/281,474, filed Oct. 26, 2011, issued as U.S. Pat. No. 8,707,483, each of which is hereby incorporated by reference herein in its entirety.

BACKGROUND

The present disclosure relates to patient support apparatuses such as hospital beds having bed frames and patient support surfaces or mattresses that are supported by the bed frames. More particularly, the present disclosure relates to a therapy enabler system for patient support apparatuses.

Hospital beds having mattresses, which are sometimes referred to as patient support surfaces or simply support surfaces, supported by bed frames are known. Some patient support surfaces are configured to provide one or more therapies to a patient such as, for example, continuous lateral rotation therapy (CLRT), alternating pressure therapy, percussion and/or vibration therapy, low air loss therapy, and so on. Oftentimes, these different types of therapies are accomplished by inflating and deflating particular air bladders of the support surface or by specialized operation of a pneumatic control system of the support surface or bed frame. Some bed frames have portions that move to provide one or more therapies such as, for example, by having upper frames or decks that rotate side to side to provide continuous lateral rotation therapy.

Some hospital bed frames have integrated pneumatic control systems that are operated to control the inflation of air bladders in a mattress. For example, the TOTALCARE® bed and VERSACARE® bed marketed by Hill-Rom Company, Inc. have integrated pneumatic control systems. Support surfaces which have different types of air bladder configurations that provide various types of therapies or functions may be supported at different times on hospital bed frames having integrated pneumatic control systems. Accordingly, information regarding the type of support surface supported on the bed frame at any given time needs to be provided to the pneumatic control system so that the pneumatic control system is operated properly to control inflation of the various air bladders of the associated mattress.

SUMMARY

The present invention comprises one or more of the features recited in the appended claims and/or the following features which, alone or in any combination, may comprise patentable subject matter:

A patient support apparatus may have a patient support structure that may be configured to support a patient in a recumbent position. The patient support structure may be configured to provide at least one therapy to a patient. The patient support apparatus may further have a therapy enabler token that may be coupleable to the patient support structure. The at least one therapy may be disabled when the therapy enabler token is decoupled from the patient support structure and the at least one therapy may be enabled in response to the therapy enabler token being coupled to the patient support structure.

In some embodiments, the patient support structure may have a token-receiving opening into which the therapy enabler token is inserted to couple the therapy enabler token to the patient support structure. The patient support structure may include a bed frame which may include a footboard. The token-receiving opening may be provided in the footboard. In some embodiments, the token-receiving opening may be provided about mid-way between opposite sides of the footboard and nearer to a bottom of the footboard than to a top of the footboard. The token-receiving opening may comprise a horizontally oriented slot, for example. In some embodiments, the bed frame may include a siderail and the token-receiving opening may be provided in the siderail. In some embodiments, the bed frame may include a headboard and the token-receiving opening may be provided in the headboard.

Alternatively or additionally, the patient support structure may include a mattress. The token-receiving opening may be provided in the mattress. In some embodiments, the token-receiving opening may be provided in a sidewall of the mattress. If desired, the token-receiving opening may be provided near a foot end of the mattress.

In some embodiments, the patient support structure may have a hand-held controller pendant that includes a token-receiving opening into which the therapy enabler token is inserted to couple the therapy enabler token to the patient support structure. Alternatively or additionally, the patient support structure may have a graphical user interface that includes a token-receiving opening into which the therapy enabler token is inserted to couple the therapy enabler token to the patient support structure.

According to this disclosure, the therapy enabler token may have a transmitter and the patient support structure may have a receiver that receives a wireless transmission from the transmitter to enable the at least one therapy when the transmitter is within reception range of the receiver. In other embodiments, the therapy enabler token may physically connect to the circuitry of the patient support structure. In some embodiments, the therapy enabler token may be configured to be worn by the patient. For example, the therapy enabler token may be included as part of a wristband to be worn on the patient's wrist or may be part of, or attached to, a gown or other type of garment worn by the patient. In some embodiments, mechanical coupling of the therapy enabler token to the patient support structure enables the at least one therapy without any data transfer. In some such embodiments, therefore, the therapy enabler token may be a key.

According to this disclosure, the patient support structure may include a token reader that reads information stored on the therapy enabler token when the therapy enabler token is placed adjacent the reader. Thus, it is contemplated by this disclosure that the therapy enabler token may include a memory device that may be read in response to being inserted into an opening associated with the reader. The memory device may comprise at least one of an RFID device, a serial data transfer device, a resistor network, a ROM chip, an EPROM chip, or an EEPROM chip, just to name a few examples.

Further according to this disclosure, the patient support structure may include a bed frame supporting a pneumatic control system. The patient support structure may also include a mattress supported by the bed frame and having at least one air bladder the inflation of which may be controlled by the pneumatic control system in connection with the at least one therapy when the therapy enabler token is coupled to the patient support structure. In some embodiments, the at least one air bladder may also be inflated by the pneumatic control system for the general support of the patient when the therapy enabler token is decoupled from the patient support structure. Alternatively or additionally, the mattress may have at least one patient support air bladder the inflation of which is controlled by the pneumatic control system regardless of whether the therapy enabler token is coupled to the patient support structure.

The at least one therapy associated with the at least one air bladder may include at least one of continuous lateral rotation therapy, percussion therapy, vibration therapy, alternating pressure therapy using interdigitated air bladders, alternating pressure therapy using zoned air bladders (sometimes referred to as "opti-rest"), low air loss therapy, microclimate management therapy, and sequential compression therapy. In the alternating pressure embodiments, the bladders that are sequentially inflated and deflated to provide the therapy when the therapy enabler token is coupled to the patient support structure are also inflated for general patient support when the therapy enabler token is decoupled from the patient support structure.

The patient support structure may include a bed frame that may have movable portions the movement of which may provide the at least one therapy. For example, the movable portions of the bed frame may be rotated from side to side to provide continuous lateral rotation therapy.

According to this disclosure, the patient support structure may include a control system configured for communication with a remote computer via a network of a healthcare facility. The therapy enabler token may be reprogrammable by the remote computer when the therapy enabler token is electronically coupled to the patient support structure. The therapy enabler token may include parameters or software code or both that may be downloaded to a control system of the patient support structure for use in controlling the therapy delivered to the patient.

In some embodiments, the therapy enabler token may be reprogrammable when the therapy enabler token is separated from the patient support structure. For example, the therapy enabler token may be configured to be reprogrammable with wireless signals. As another example, the therapy enabler token may couple to a computer or a docking station associated with a computer for reprogramming.

In some embodiments according to this disclosure, the patient support structure may include a first microcontroller and the therapy enabler token may include a second microcontroller that communicates with the first microcontroller when the therapy enabler token is electronically coupled to the patient support structure. At least one of an operational parameter and a permission code may be read by the first microcontroller from at least one address of the second microcontroller. For example, the at least one address read by the first microcontroller may comprise a message object's address.

According to this disclosure, the therapy delivered to the patient may be controlled based on a patient profile. The patient profile may include information regarding at least one of the patient's height, weight, age and sex, just to name a few examples of the type of information that may be included the patient profile. The patient support structure may be configured to receive at least some of the patient profile from an electronic medical records system (EMR). Alternatively or additionally, the patient support structure may be configured to determine at least some of the patient profile based on a signal from at least one sensor of the patient support structure.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION

Figure 1:
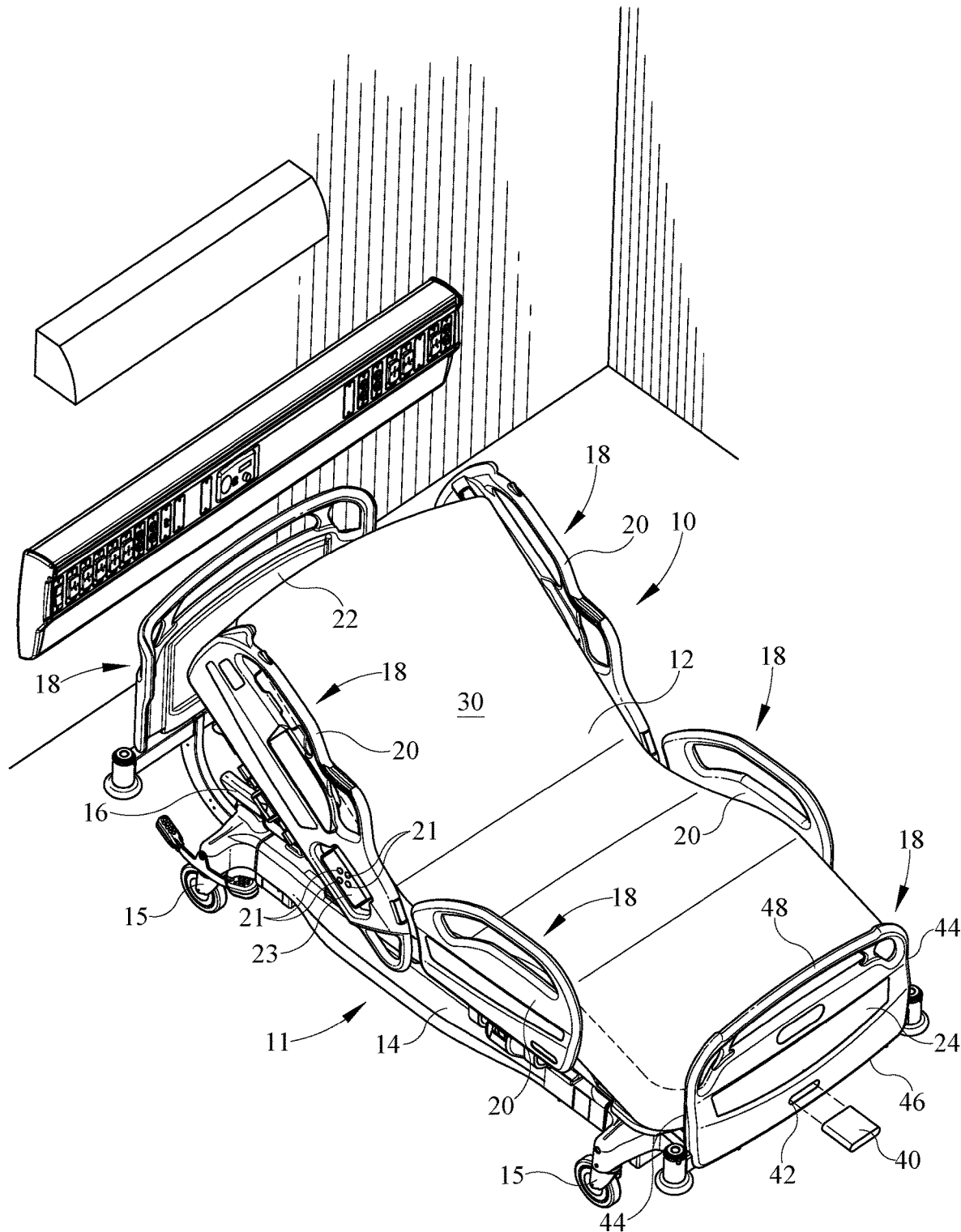
FIG. 1 is a perspective view showing a patient support structure including a bed frame and a support surface supported on the bed frame and showing a therapy enabler token arranged for insertion into an opening provided in a footboard of the bed frame.

A patient support apparatus or bed 10 includes a bed frame 11 and a patient support surface or mattress 12 as shown in FIG. 1. Bed frame 11 and patient support surface 12, either individually or collectively, are considered to be a patient support structure according to this disclosure. Bed frame 11 includes a base frame 14 with casters 15, an upper frame 16 supported above base frame 14 by an elevation mechanism (not shown), and a set of barriers 18 which, in the illustrative example, includes a set of siderails 20, a headboard 22, and a footboard 24. Mattress 12 is supported atop an articulating deck (not shown) as is well-known in the art.

Apparatus 10 has a user interface or control panel 23 with buttons 21 that are pressed to control various functions of bed 10 such as the deck articulation functions and support surface functions. In some embodiments, control panel 23 comprises a graphical user interface that serves as a control panel for accepting user inputs for the control of the various bed functions. In some embodiments, control panel 23 is detachable from siderail 20 and serves has a hand-held pendant for the control of the various functions of bed 10. In some such embodiments, the control panel 23 is tethered to siderail 20 via a communication cord or cable and in other such embodiments, the control panel 23 communicates wirelessly with the other components of the control system of bed 10.

Figure 7:
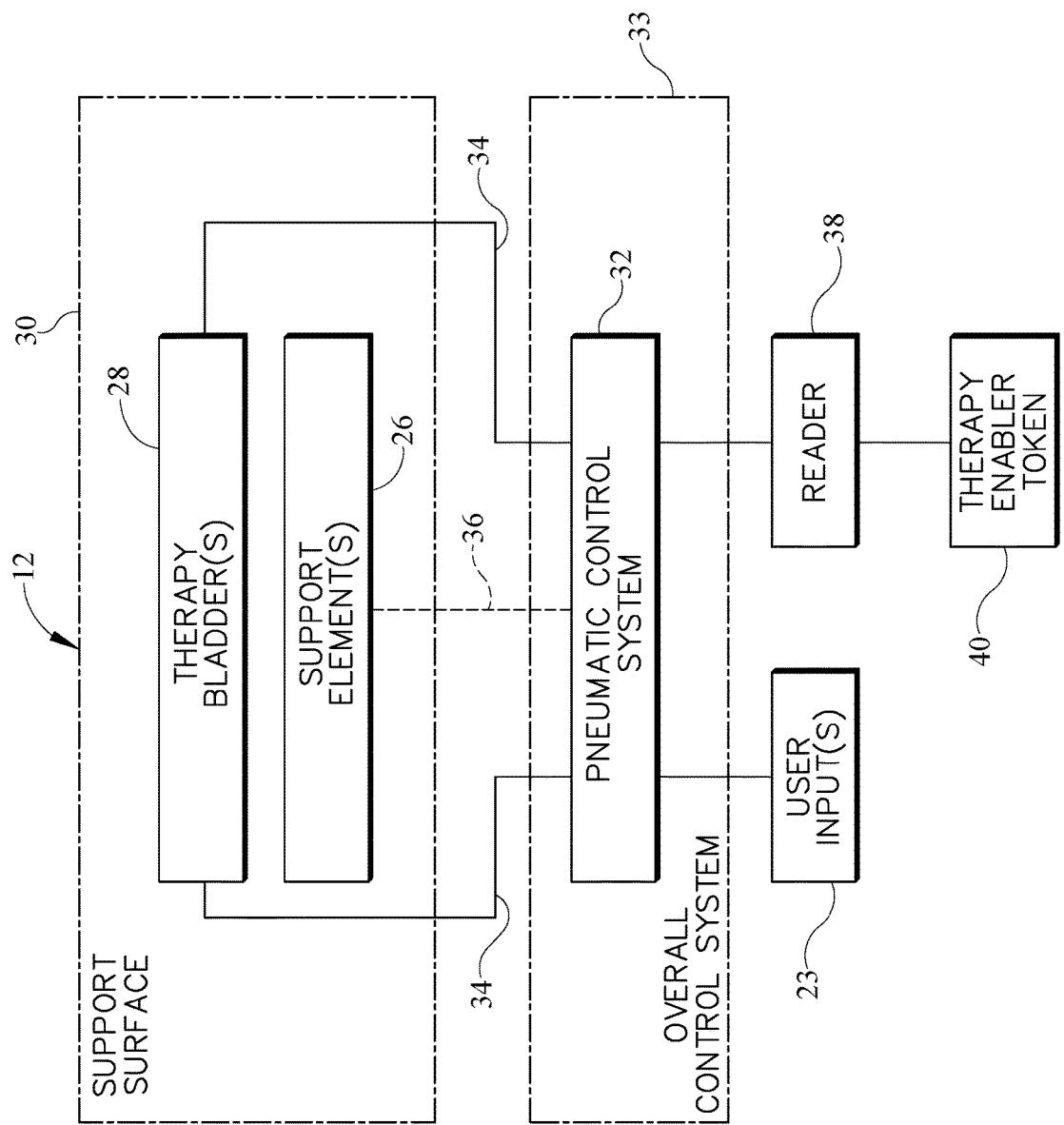
FIG. 7 is a block diagram showing aspects of a support surface and a pneumatic control system.

Support surface 12 includes one or more support elements 26 such as air bladders or foam elements and one or more therapy bladders 28 as shown diagrammatically in FIG. 7. In some embodiments, the support elements 26 also serve as therapy bladders such that separate therapy bladders 28 are omitted in such embodiments, or vice versa. In other words, it is within the scope of this disclosure for mattress 12 to have air bladders that serve both as general patient support bladders and as therapy bladders. Optionally, elements 26 and bladders 28 are encased in a cover 30 as is the case in the illustrative embodiment of surface 12.

A pneumatic control system 32 controls the inflation and deflation of the therapy bladders 28 via one or more pneumatic lines 34. In those embodiments in which support elements 26 comprise one or more air bladders, pneumatic control system also controls the inflation and deflation of those air bladders via one or more pneumatic lines 36 as suggested in FIG. 7. In some embodiments, pneumatic control system 32 is integrated into or included as part of bed frame 11 and receives input signals from user interface 23. Thus, pneumatic control system 32 may be included as part of an overall control system 33 of the patient support structure which is comprised of bed frame 11, support surface 12, or both as indicated diagrammatically in FIG. 7 (in phantom).

According to this disclosure, the therapy function or functions of surface 12 provided by the cooperation of pneumatic control system 32 with one or more bladders 28 (or bladders 26 in some embodiments) is disabled unless a therapy enabler token 40 is coupled, either mechanically or electronically or both, to the patient support structure. In some contemplated embodiments, the therapy function(s) of the patient support structure is disabled unless a reader 38 is in electronic communication with a therapy enabler token 40 as shown diagrammatically in FIG. 7. In other contemplated embodiments, token 40 operates akin to a mechanical key to enable the therapy function(s) of the patient support structure. However, the ability of control system 32 to inflate and deflate support element(s) 26 remains enabled or operational in those embodiments in which support element(s) 26 comprise one or more air bladders regardless of whether or not token 40 is in communication with reader 38.

The at least one therapy associated with the at least one air bladder 28 includes at least one of continuous lateral rotation therapy, percussion therapy, vibration therapy, alternating pressure therapy using interdigitated air bladders, alternating pressure therapy using zoned air bladders (sometimes referred to as "opti-rest"), low air loss therapy, microclimate management therapy, and sequential compression therapy. In the alternating pressure embodiments, the bladders 28 that are sequentially inflated and deflated to provide the therapy when the therapy enabler token 40 is coupled to the patient support structure are also inflated for general patient support when the therapy enabler token 40 is decoupled from the patient support structure. In the example of sequential compression therapy, the at least one air bladder 28 is configured as a sequential compression therapy garment, such as a wrap, sleeve, or boot, that is worn on a patient's limb.

Therapy enabler token 40 can take on a variety of forms and communicate with reader 38 according to different technologies according to this disclosure. However, it is contemplated by this disclosure that token 40 is sufficiently small and compact enough to be carried easily by a caregiver and placed in a shirt pocket, lab coat pocket or pants pocket. Thus, tokens 40 are sized similarly to Universal Serial Bus (USB) sticks, cell phones, or credit cards for example, although it is within the scope of this disclosure for tokens 40 to be smaller than, or larger than, these types of devices as long as tokens 40 are sufficiently small to be carried easily by a caregiver and placed in a garment pocket.

Furthermore, the various tokens 40 of some embodiments contemplated by this disclosure include memory devices or components contained within or mounted to a housing or substrate of some sort, but are devoid of pneumatic components such as valves, conduits, manifolds, pumps, compressors, and the like. Thus, the tokens 40 contemplated by this disclosure are not like the therapy modules used, for example, on Hill-Rom's TotalCare® bed and shown and described in U.S. Pat. Nos. 6,047,424 and 6,119,291 or the compression sleeve modules shown and described in U.S. Pat. No. 7,641,623, which modules have both electrical and pneumatic components and which are too large to fit into a pocket of the typical garments worn by a caregiver. Also, the various tokens 40 contemplated by this disclosure are devoid of any buttons or other user inputs and so are not like the user interface modules shown and described in U.S. Pat. No. 7,849,545. The memory components or devices included as part of tokens 40 include for example, a magnetic strip encoded with information, an RFID device, a serial data transfer device (e.g., an iButton™ device of the type available from Maxim Integrated Products), a resistor network, a ROM chip, an EPROM chip, or an EEPROM chip, just to name a few examples.

Referring again to FIG. 1, foot board 24 has an opening 42 that is sized and configured to receive therapy enabler token 40 therein. In some embodiments, only a portion of token 40 is inserted into opening 42 such that enough of token 40 projects outwardly from opening 42 so as to be grippable by a caregiver and removed from opening 40. In the illustrative embodiment, opening 42 is located about mid-way between opposite sides 44 of footboard 24 and nearer to a bottom 46 of footboard 24 than to a top 48. It is within the scope of this disclosure, however, for opening 42 to be provided at other locations on footboard 24. In the illustrative example, opening 42 is formed as a horizontally oriented slot. However, it should be understood that opening 42 may be shaped or oriented differently in other embodiments, such as being oriented vertically for example.

Insertion of token 40 into opening 42 electronically couples the token 40 with the patient support structure, or more specifically, to the pneumatic control system 32 via reader 38 in the illustrative example. In those embodiments in which token 40 has a magnetic strip encoded with information, reader 38 comprises a magnetic strip reader. In those embodiments in which token 40 carries a memory chip or a resistive network, then reader comprises a first electrical port or coupler that electrically couples to a second electrical port or coupler provided on the token, along with any circuitry for reading data off of token 40 into memory associated with reader 38 or system 32 or system 33, as the case may be. In those embodiments in which token 40 communicates wirelessly, such as via RFID or induction, then reader comprises a wireless receiver or transceiver of the appropriate type to receive data output wirelessly from token 40.

Based on the foregoing, it should be understood that, in some embodiments, all of the components of reader 38 are housed in, or carried by, footboard 24 and, in other embodiments, footboard 38 houses or carries only a portion of the components that together are considered to be reader 38. Furthermore, in those embodiments in which footboard 24 is removable from upper frame 16 of bed frame 11, it will be appreciated that an electrical connector is included in an electrical path between reader 38 and system 32 (or system 33) or in an electrical path between components of reader 38 in those embodiments in which some components of reader 38 are carried by footboard 24 and other components of reader 38 are carried elsewhere on bed 10 such as on upper frame 16. Alternatively or additionally, headboard 22 has a token-receiving opening that is substantially similar to opening 42 provided in footboard 24 as discussed above. The discussion above regarding token-receiving opening 42 in footboard 24 is equally applicable to headboard 22 in those embodiments in which a token-receiving opening is provided in headboard 22.

Once token 40 is properly inserted into opening 42, in some embodiments, information is transferred from the token 40 to the pneumatic control system 32 to enable the therapy that is delivered to an associated patient. The information may be as simple as an enablement code (aka a permission code) that is recognized by system 32 to enable the therapy. Alternatively or additionally, in some embodiments, the information may include operational parameters that are used by system 32 in connection with the delivery of the associated therapy or therapies to the patient. Further alternatively or additionally, in some embodiments, the information transferred from token 40 to system 32 includes some or all of the software code that is executed by system 32 in connection with delivery of the associated therapy or therapies to the patient.

According to some embodiments contemplated by this disclosure, control system 33 of the patient support structure includes a first microcontroller and token 40 includes a second microcontroller that communicates with the first microcontroller when token 40 is electronically coupled to the patient support structure. In such embodiments, at least one operational parameter or permission code is read by the first microcontroller from at least one address of the second microcontroller. The address read by the first microcontroller includes a message object's address in some embodiments. In some embodiments, the therapy delivered to the patient by the patient support structure is controlled based on a patient profile. The patient profile includes information regarding the patient's height, weight, age and sex, for example. In some embodiments, the patient support structure is configured to receive at least some of the patient profile from an electronic medical records (EMR) system. Alternatively or additionally, the patient support structure is configured to determine at least some of the patient profile based on a signal from at least one sensor of the patient support structure, such as one or more load cells of a weigh scale system of bed frame 11, for example.

Figure 2:
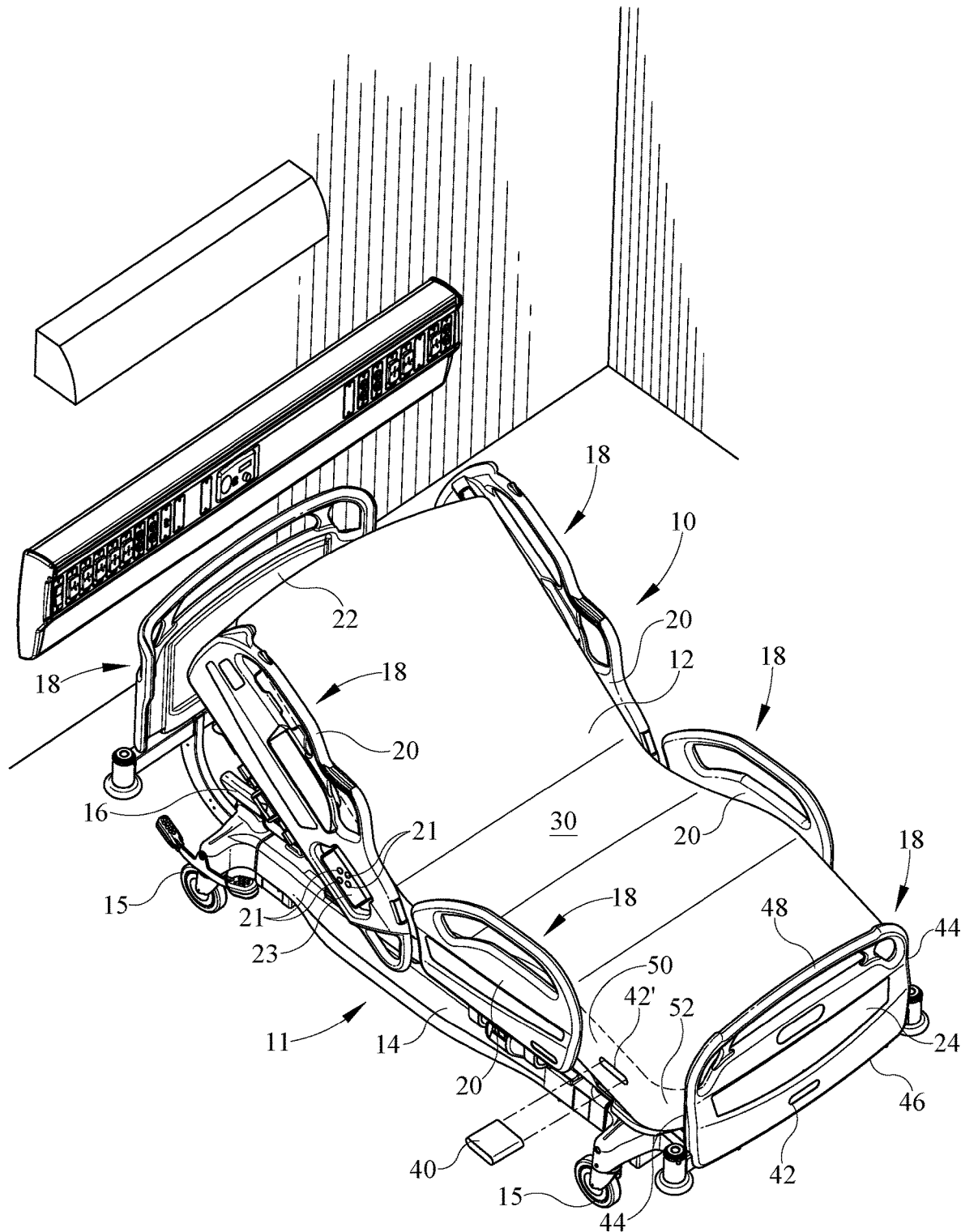
FIG. 2 is a perspective view showing an alternative embodiment, similar to the patient support structure of FIG. 1, but having a therapy enabler token arranged for insertion into an opening provided in the support surface.

Referring now to FIG. 2, an alternative embodiment is shown in which mattress 12 has an opening 42' in a sidewall 50 for receipt of token 40. In the illustrative example, the token-receiving opening 42' is provided near a foot end 52 of mattress 12. In accordance with the example of FIG. 2, some or all of reader 38 and/or some or all of pneumatic control system 32 may be situated within an interior region (e.g., inside a spaced defined by cover 30) of mattress 12. However, it is within the scope of this disclosure for electrical lines to extend from opening 42' to reader 38 that is carried on bed frame 11 outside of mattress 12. In such embodiments, therefore, opening 42' serves as a port through which data is transferred to the reader 38 via the electrical lines that are routed, at least partially, through the mattress. In more typical embodiments, however, the reader 38 and at least some portion of the pneumatic control system 32 resides within mattress 12. Insertion of token 40 into opening 42' permits information of the type described above to be provided to system 32. As was the case with opening 42, opening 42' may have different orientations, sizes, and shapes in other embodiments.

Figure 3:
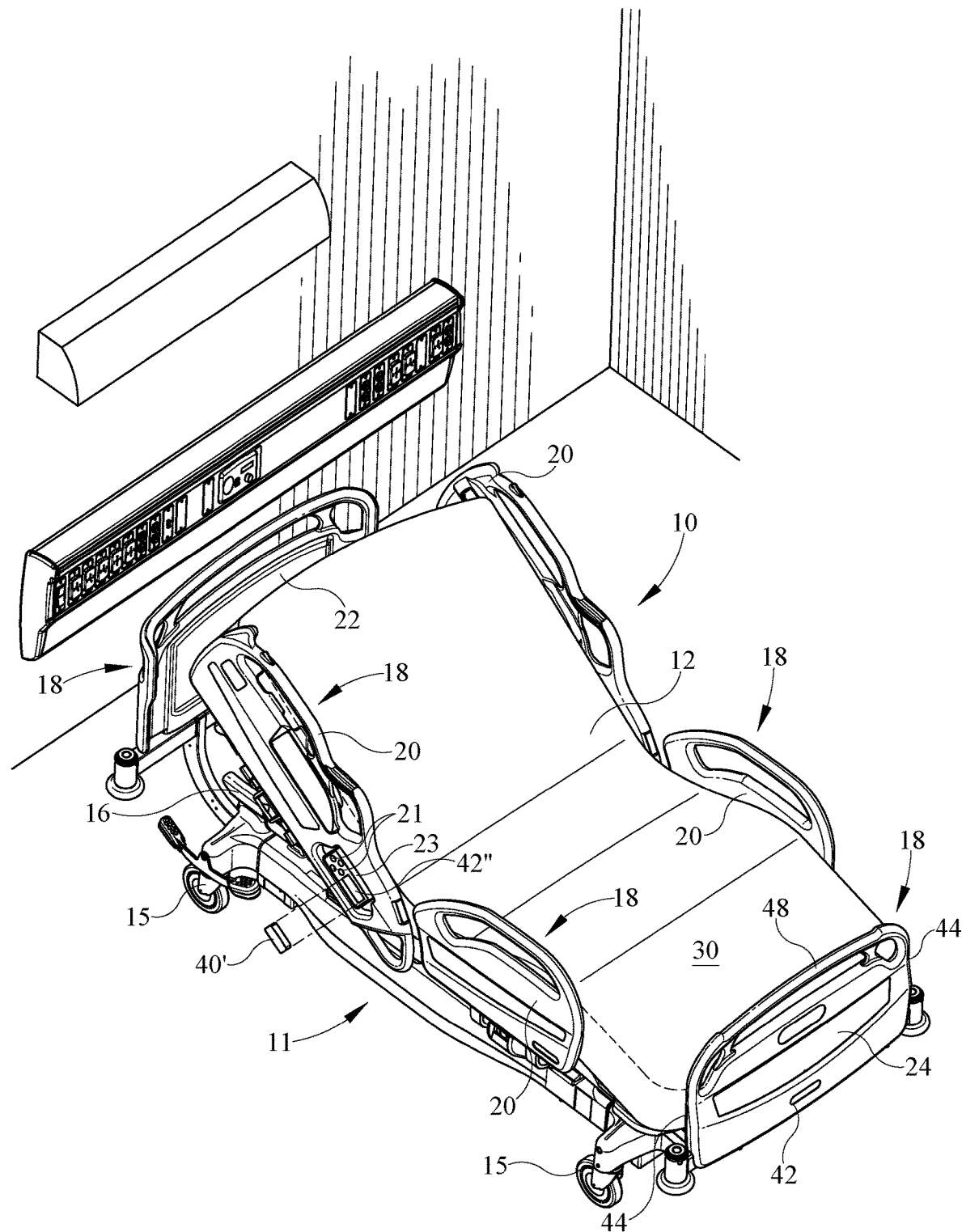
FIG. 3 is a perspective view showing another alternative embodiment, similar to the patient support structures of FIGS. 1 and 2, but having a therapy enabler token arranged for insertion into an opening provided in a siderail of the bed frame.

Referring now to FIG. 3, another alternative embodiment is shown in which control panel 23 has an opening 42" that is configured to receive a token 40' therein. In other embodiments, opening 42" is provided in one or more of siderails 20 at a location other than the control panel 23. Also, according to the illustrative example, token 40' is inserted into opening 42" in a widthwise manner which is in contrast to the lengthwise insertion of token 40 into openings 42, 42' in the FIGS. 1 and 2 examples, respectively. In some embodiments, an outwardly facing surface of token 40' is substantially flush or coplanar with an outwardly facing surface of control panel 23 but this need not be the case. In some such embodiments, an ejector button or lever (not shown) is provided for use in pushing token 40' out of opening 42". In other embodiments, one or more finger-receiving recesses is provided along one or more of the top, bottom or sides of opening 42" to permit a caregiver to manually remove token 40' from opening 42".

In accordance with the embodiment of FIG. 3, some or all of the components of reader 38 are housed within or coupled to the associated siderail 20 that includes control panel 23 having opening 42". The various options for the type of electrical technology employed on token 40 is equally applicable to token 40' as is the various options for the location of the various components of systems 32, 33. As mentioned above, control panel 23 comprises a graphical user interface in some embodiments. Thus, in such embodiments, opening 42" is provided in the graphical user interface, or more specifically, in a housing of the graphical user interface. As also mentioned above, control panel 23 is detachable from the associated siderail 20 and is used as a hand-held pendant for controlling functions of bed 10. Thus, in such embodiments, opening 42" is provided in the hand-held pendant.

Figure 4:
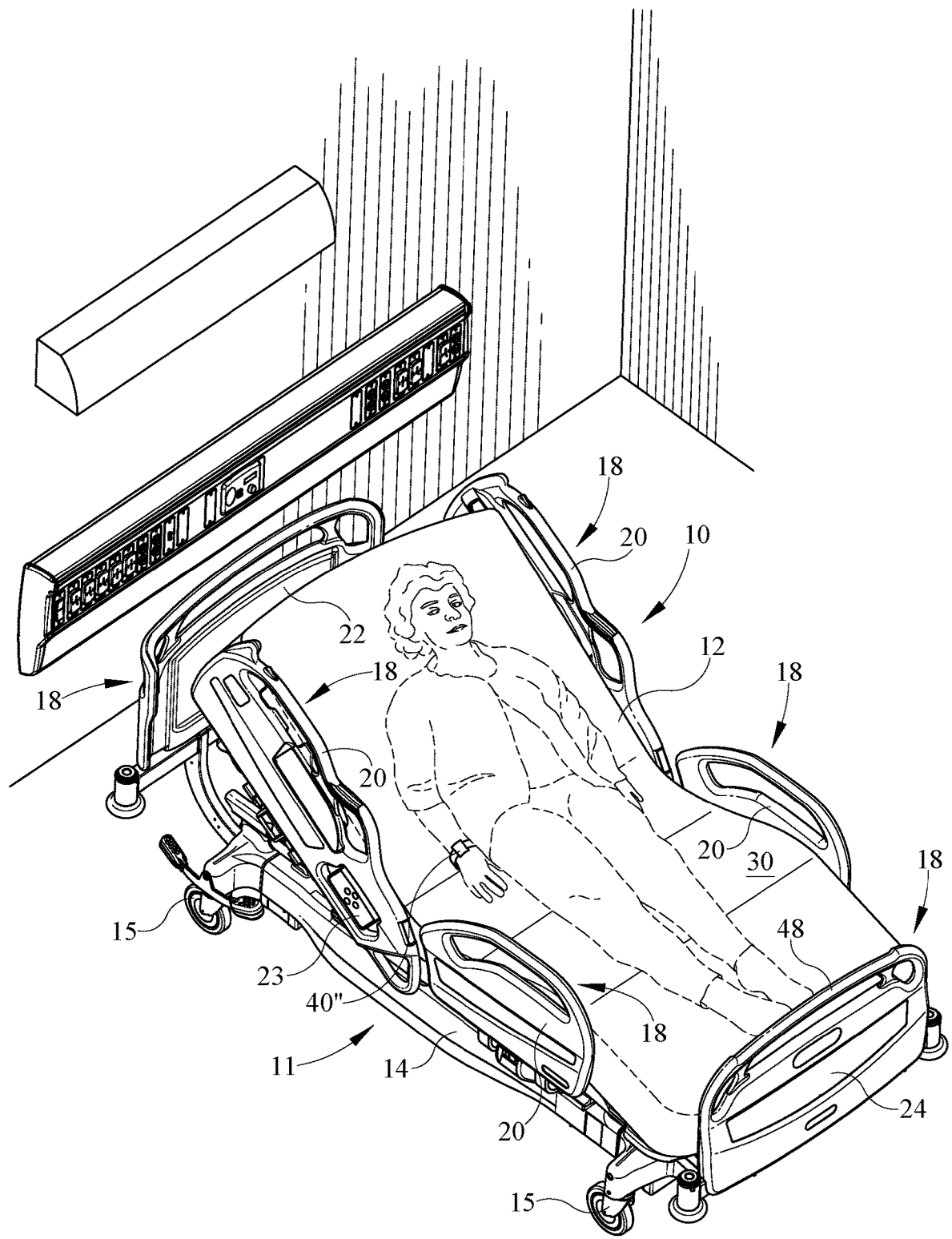
FIG. 4 is a perspective view showing a further alternative embodiment, similar to FIGS. 1-3, but having a therapy enabler token worn on the wrist of a person (shown in phantom) supported on the support surface.

Referring now to FIG. 4, yet another alternative embodiment is shown in which a token 40" is worn by the patient, such as on the patient's wrist. Token 40" communicates wirelessly with the associated reader 38 of bed 10 to provide the information carried on token 40" to the pneumatic control system 32 of bed 10. In some embodiments, the wireless technology employed on token 40" is short range radio frequency (RF) technology such that token 40" is in wireless communication with the reader 38 of bed 10, but not with the readers 38 of any other beds that may also be within the same hospital room. In other embodiments, token 40" employs some other wireless technology such as acoustic technology (e.g., ultrasound) or infrared (IR) technology, just to name a couple possibilities.

By providing token 40" on the patient's wrist, the therapy or therapies that are enabled by token 40" are enabled when the patient wearing token 40" moves from one bed to another, assuming that each bed has a mattress 12 and pneumatic control system 32 capable of delivering the types of therapy or therapies enabled by token 40". In the FIG. 1-3 examples described above, a caregiver needs to move the token 40, 40' from one bed 10 to another if the patient switches beds which may occur, for example, if the patient moves from a room in the intensive care unit (ICU) to a regular patient room.

In the FIG. 4 embodiment, reader 38 comprises a wireless receiver of some sort depending upon the type of wireless communication technology employed. If IR technology is used then the need for line of sight between token 40" and the reader 38 for at least a threshold amount of time for data transfer suggests that the inwardly facing upper region of any of barriers 18 is a suitable location for reader 38. If acoustic or RF technologies are used, then the reader 38 may be located just about anywhere on bed 10 and still be able to receive wireless signals from token 40". Accordingly, having reader 38 co-located with the circuitry of one of systems 32, 33 is contemplated by this disclosure. In some embodiments, instead of having token 40" included as part of a wristband worn on the patient's wrist, the therapy enabler token 40" may be included as part of, or attached to, a gown or other type of garment worn by the patient. The discussion above regarding having token 40" worn on the patient's wrist is equally applicable to having token 40" included as part of a gown or garment that is worn on any other portion of a patient's body.

Figure 5:
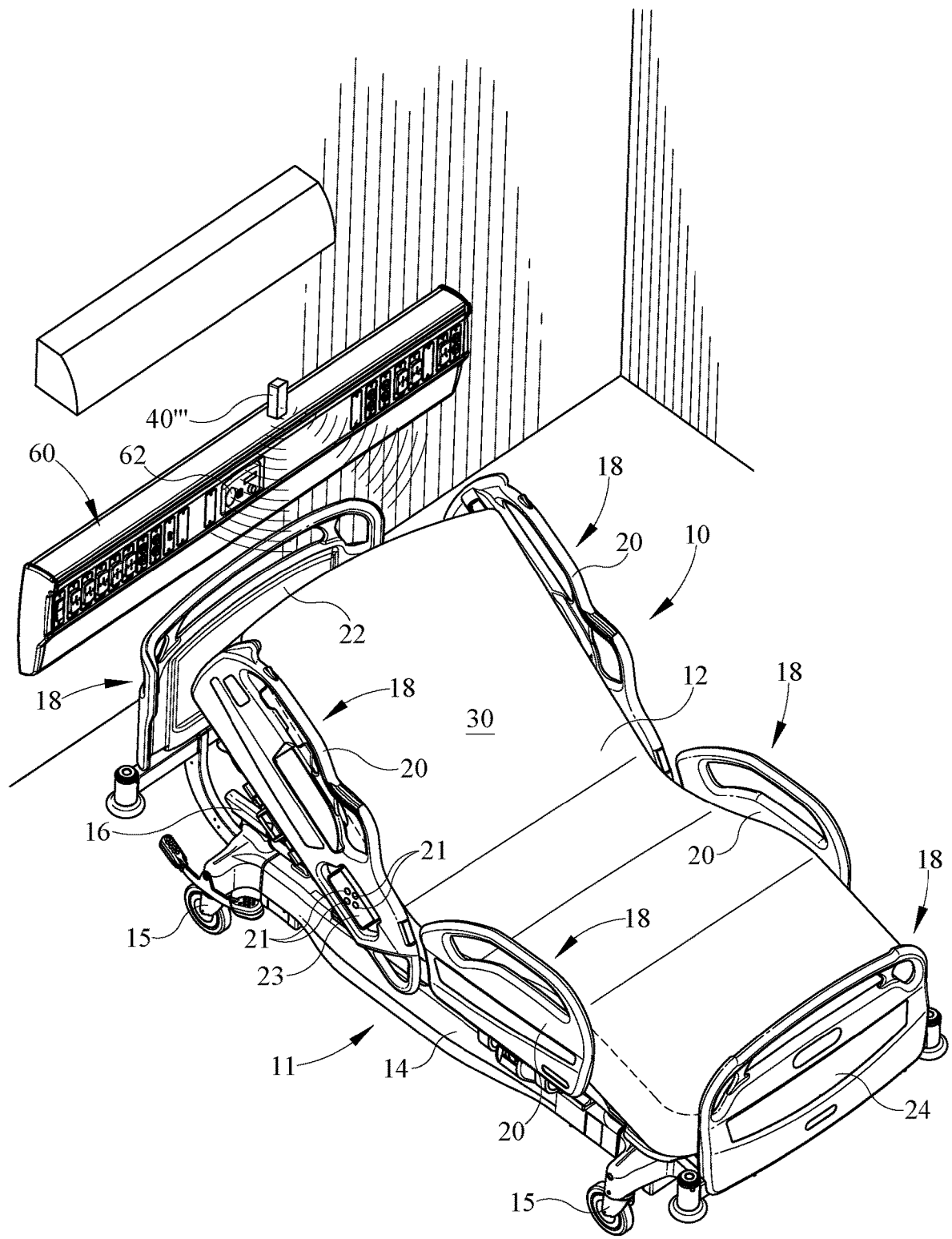
FIG. 5 is a perspective view showing yet another alternative embodiment, similar to FIGS. 1-4, but having a therapy enabler token supported on a head wall unit in a patient room and communicating wirelessly with the patient support structure.

Referring now to FIG. 5, still another embodiment is shown in which a token 40''' is located sufficiently close to bed 10 so as to communicates wirelessly with the associated reader 38. In the illustrative example, token 40''' is resting atop a headwall unit 60. It should be appreciated that token 40''' simply needs to be in close enough proximity with bed 10 to communicate wirelessly with the associated reader 40 and so may be supported on other structures such as a nightstand near the bed, on a shelf that is not part of a head wall unit but that is sufficiently close to bed 10, on a window sill, or even on a floor of the room, just to name a few of the possibilities. The discussion above regarding the type of wireless technologies used for different embodiments of token 40" is equally applicable to token 40'.

The location of reader 38 on bed 10 of the FIG. 5 example is on the outwardly facing side of headboard 22 in some embodiments, such as with regard to embodiments employing IR communication technology. Optionally, several readers 38 comprising IR receivers may be provided at various locations on bed 10, such as on the outwardly facing sides of each of barriers 18, if desired, to increase the options for locating token 40' around the periphery of bed and still achieving suitable wireless communication with system 32 via one or more of such readers 38. As was the case with regard to token 40", if token 40' employs ultrasound or short range RF technology, then reader 38 may be located anywhere on bed 10, as desired.

According to a variant of the FIG. 5 example, headwall unit 60 has an audio station 62 mounted thereto and reader 38 is included in audio station 62. Audio station 62 is part of a nurse call system as is known in the art. In some embodiments, audio station 62 is a graphical audio station having a touch screen display. See, for example, U.S. Pat. Nos. 7,746,218; 7,538,659; 7,319,386; 7,242,308; 6,897, 780; 6,362,725; 6,147,592; 5,838,223; 5,699,038 and 5,561, 412 and U.S. Patent Application Publication Nos. 2009/ 0217080; 2009/0214009; 2009/0212956; and 2009/ 0212925, all of which are hereby incorporated by reference herein in their entirety for all that they teach. It is common to connect hospital beds to a nurse call system via a communication cable. In some arrangements, the communication cable outlet or port to which such nurse call communication cables connect are electrically coupled to the audio station in the room and then the audio station is electrically coupled, such as a via a network (e.g., a local area network (LAN), wide area network (WAN), or ethernet) to one or more remote computer devices of the nurse call system.

Based on the foregoing, it is within the scope of the present disclosure for bed 10 to be in electrical communication with audio station 62. Thus, information from token 40' provided wirelessly to the reader 38 associated with audio station 62 is communicated to system 32 of bed 10, such as via the nurse call cable mentioned above, in order to enable one or more therapies of bed 10. It is also within the scope of this disclosure for the information received from token 40''' by reader 38 of audio station 62 to be communicated by audio station 62, along with other data such as location data and bed status data, to a remote computer of the nurse call system or of any other system for that matter. The remote computer then processes the information from token 40''' to verify that the patient assigned to bed 10 at the corresponding location is to receive the therapy that is enabled by token 40'''. If the type of therapy enabled by token 40' is contraindicated for the patient assigned to bed 10 for the particular location (e.g., rotation therapy is typically contraindicated for a patient recovering from spinal surgery), then a warning message or alert is displayed at one or more of the remote computer, the audio station 62, and a graphical display screen on bed 10. Alternatively or additionally, the warning message or alert is transmitted to a wireless communication device, such as a pager device or voice communication device, carried by one or more caregivers that are assigned to the patient.

Figure 6A:
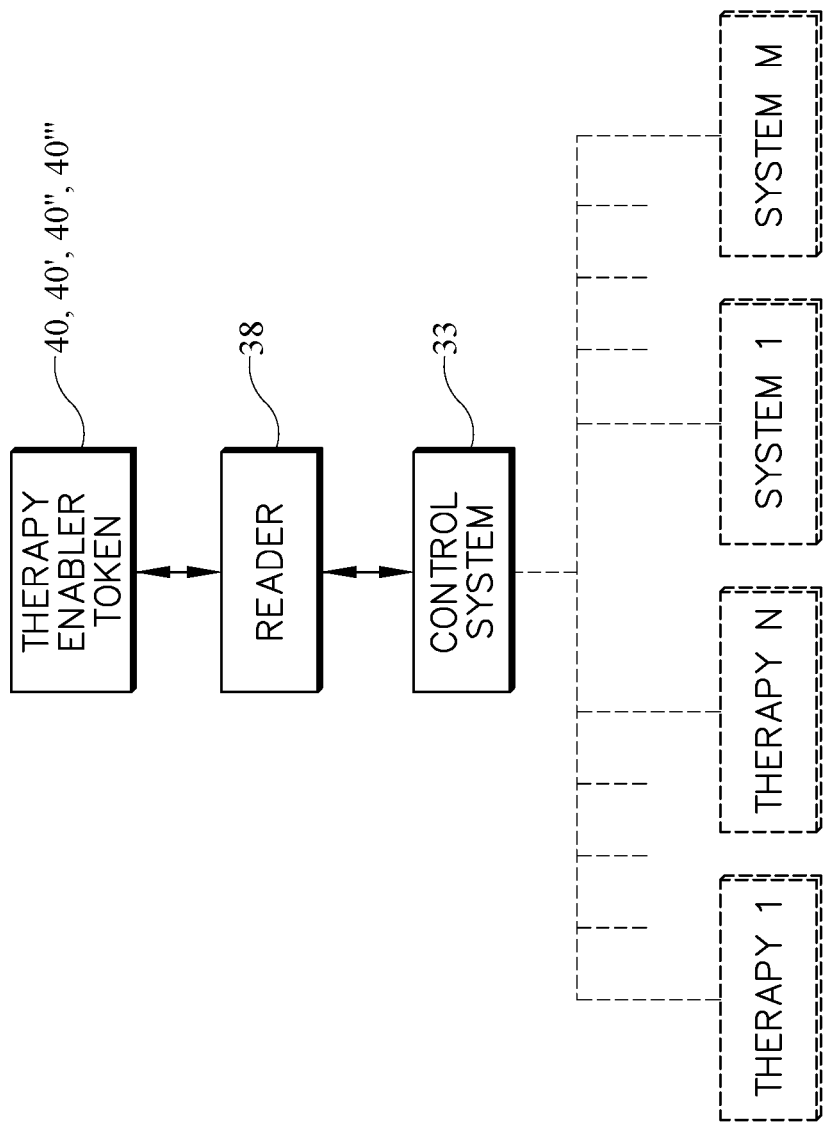
FIG. 6A is a block diagram showing a first system architecture in which a therapy enabler token communicates with a reader coupled to a control system that controls operation of therapies 1-N and systems 1-M.

Referring now to FIGS. 6A-6F, various system architectures are shown diagrammatically. FIG. 6A is a block diagram showing a first system architecture that is similar to FIG. 7. In FIG. 6A, therapy enabler token, be it token 40, 40', 40", or 40''', communicates with reader 38 which, in turn, communicates with control system 33. In FIG. 6A, the therapies enabled by the associated token 40, 40', 40", 40''' are indicated at the blocks labeled "Therapy 1" through "Therapy N," with N suggesting that it is within the scope of this disclosure for any number of therapies to be enabled by the associated token 40, 40', 40", 40'''.

Another aspect of this disclosure is also suggested in FIG. 6A. In particular, it is within the scope of this disclosure for token 40, 40', 40", or 40''' to not only enable therapy functions but, alternatively or additionally, to enable other systems or non-therapy functions of bed 10. These other systems that are enabled by respective tokens 40, 40', 40", 40''' are indicated by blocks labeled with "System 1" through "System M," with M suggesting that it is within the scope of this disclosure for any number of non-therapy functions of bed 10 to be enabled by respective tokens 40, 40', 40", 40'''. For example, in some embodiments, frame 11 of bed 10 is capable of being moved into a chair egress position to enable a patient to egress from bed 10 in much the same way that a person egresses from a standard chair. Thus, to give one example according to this disclosure, frame 11 is locked out from moving into the chair egress position unless an appropriate token 40, 40', 40", 40'" is electronically coupled to system 33 (via reader 38 in the FIG. 6A example) to enable the chair egress position function of frame 11 of bed 10.

Figure 6B:
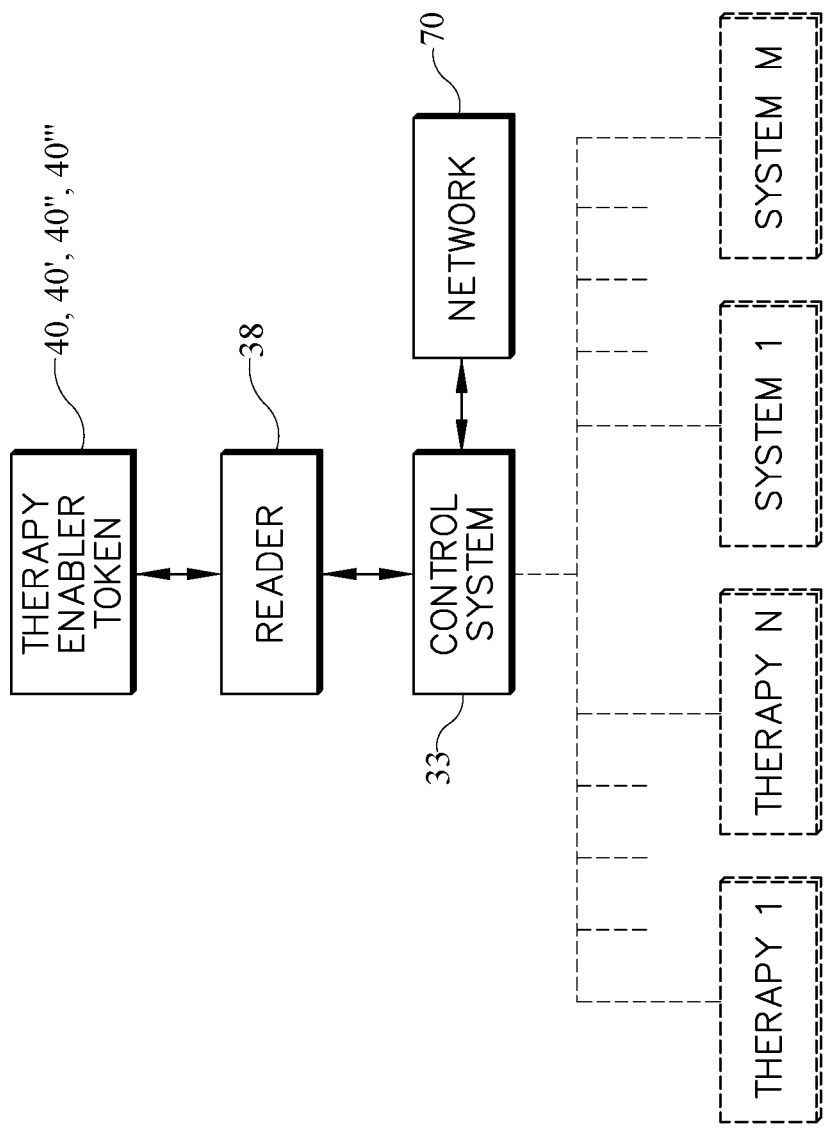
FIG. 6B is a block diagram, similar to FIG. 6A, but having the controller also in communication with a network of a healthcare facility.

In some embodiments, control system 33 is in communication with a network 70 as shown diagrammatically in FIG. 6B. Other than the addition of network 70 in communication with control system 33, FIG. 6B is the same as FIG. 6A. Thus, the discussion above with regard to FIG. 6A is equally applicable to FIG. 6B. Network 70 is intended to represent the infrastructure (e.g., wireless access ports, Ethernet jacks such as RJ-45 connectors, wires, routers, gateways, etc.) provided in a healthcare facility and the various remote computer devices (e.g., personal computers, servers, laptop computers, etc.) that are coupled to the infrastructure. Thus, the nurse call system components described above are considered to be an example of the types of components that are intended to be represented by network 70 in FIG. 6B. The computer(s) of an admission/discharge/transfer (ADT) system or an electronic medical records (EMR) system are further examples of other components or computer devices that are included in network 70 in some embodiments.

Figure 6C:
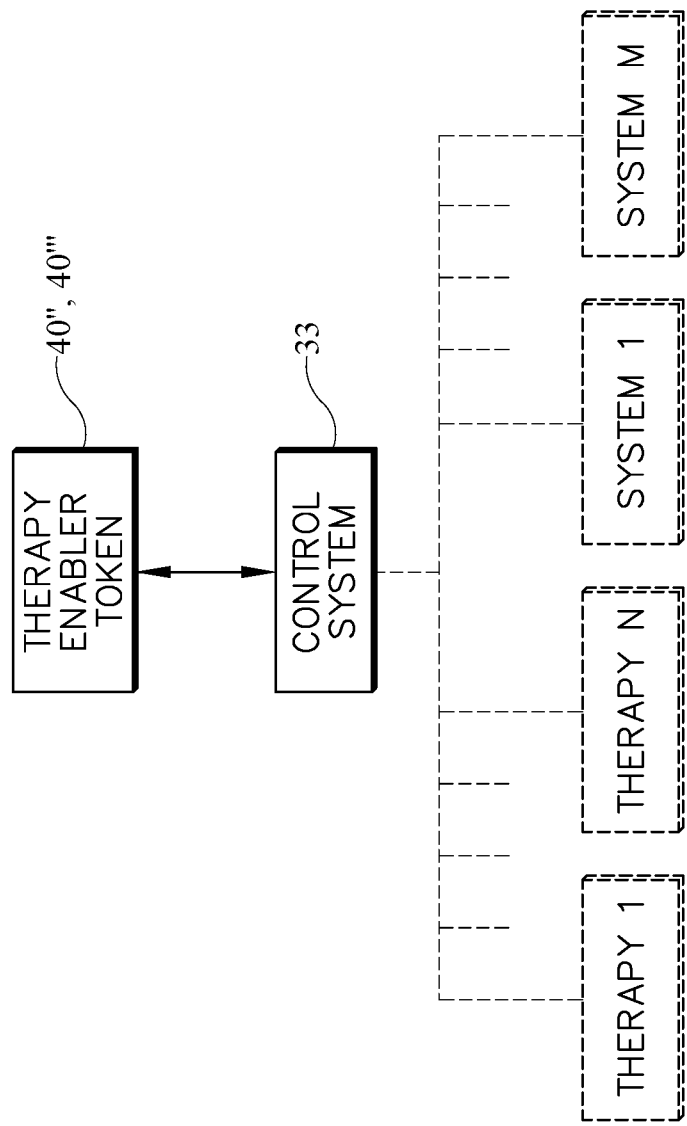
FIG. 6C is a block diagram showing a second system architecture in which a therapy enabler token communicates wirelessly with a control system.

Referring now to FIG. 6C, another system architecture is shown in which therapy enabler token 40", 40'" communicates wirelessly with control system 33. While no reader 38 block is present in FIG. 6C, it will be understood that control system 33 includes one or more electrical components that receive the wireless information emitted from token 40", 40'". Thus, FIG. 6C is illustrative of embodiments in which the reader components are co-located with, or part of, the circuitry of control system 33. It is also worth mentioning that FIGS. 6A-6C have bidirectional arrows drawn diagrammatically between the various blocks to indicate that bidirectional communication, be it wired or wireless communication, between these various components or systems is within the scope of this disclosure. Thus, it is contemplated by this disclosure that, in addition to information being transferred from token 40, 40', 40", 40'" to control system 33, information is also transferred from control system 33 to token 40, 40', 40", 40'", via reader 38 in some instances, for storage in token 40, 40', 40", 40'" in some embodiments.

Figure 6D:
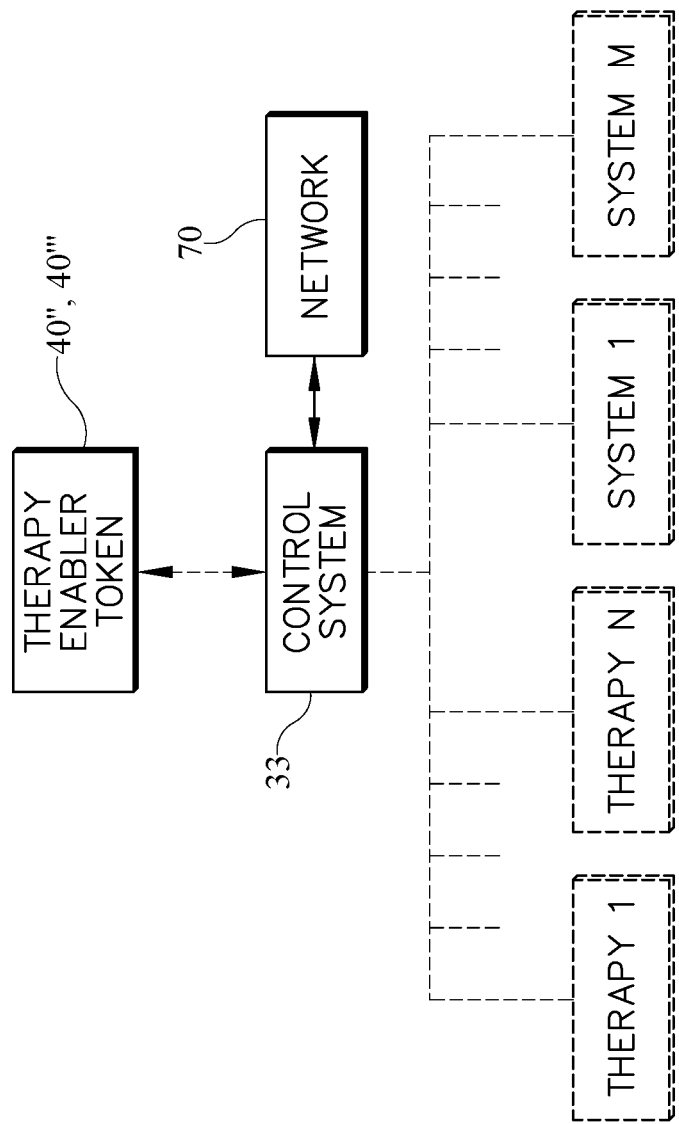
FIG. 6D is a block diagram, similar to FIG. 6C, but having the controller also in communication with a network of a healthcare facility.

In some embodiments employing wireless communication, control system 33 is in communication with a network 70 as shown diagrammatically in FIG. 6D. Other than the addition of network 70 in communication with control system 33, FIG. 6D is the same as FIG. 6C. Thus, the discussion above with regard to FIG. 6C is equally applicable to FIG. 6D. In connection with the bidirectional communication between control system 33 and token 40", 40'", it is within the scope of this disclosure for a computer device of network 70 to transmit updated software and/or operational parameters to token 40", 40'" to permit older software versions to be replaced by newer software versions, for example. Thus, when a computer included as part of network 70 is signaled by control system 33 that it is in communication with token 40", 40'", the computer of network 70 responds by transmitting the new software or operational parameters to control system 33 for subsequent transmission to token 40", 40'". A similar type of software or parameter upgrade can be accomplished as well when tokens 40, 40' are used in the Fig. B type of architecture.

Figure 6E:
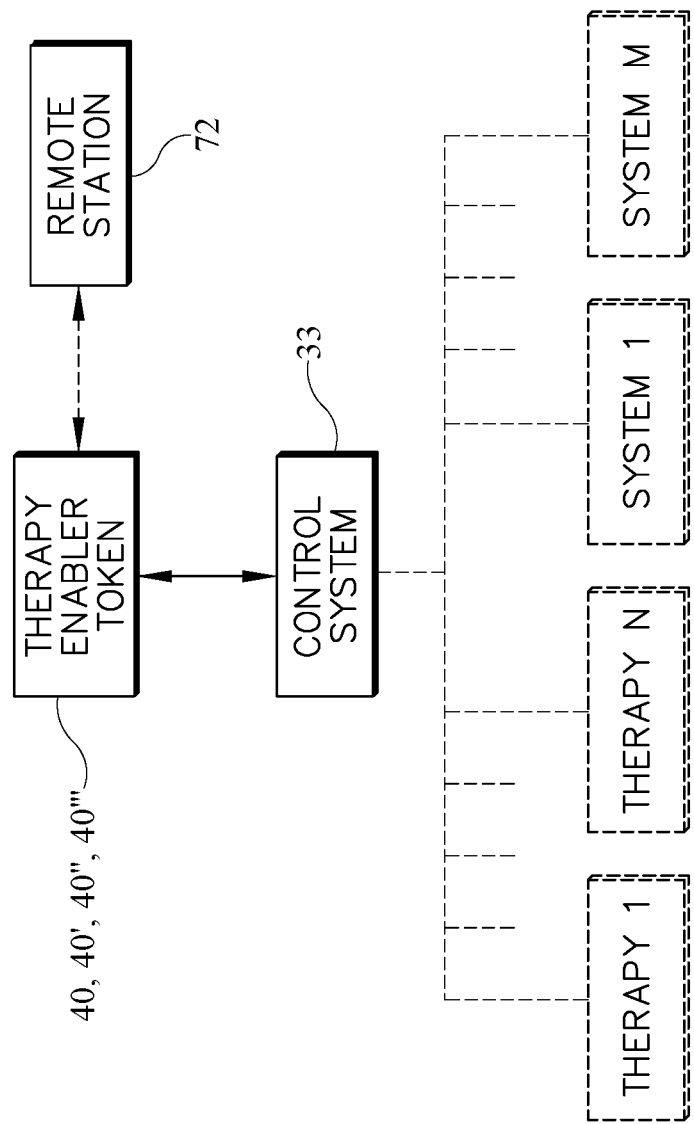
FIG. 6E is a block diagraph showing a third system architecture in which a therapy enabler token communicates with a control system and communicates wirelessly with a remote station.

Referring now to FIG. 6E, a further system architecture according to this disclosure is shown in which a therapy enabler token 40, 40', 40", 40'" communicates via a wired connection with control system 33 of bed 10 and also communicates wirelessly with a remote station 72. The remote station 72 comprises a computer, for example. Thus, in the FIG. 6E example, information is transferred wirelessly and bidirectionally between token 40, 40', 40", 40'" without involving control system 33 in the communication path. In some embodiments, a wireless access receive the wireless signals from token 40, 40', 40", 40'" in a patient room and then communicates the information to the remote station 24 via wired or wireless infrastructure. The remote station 72 is also able to send updated software or parameters to token 40, 40', 40", 40'" wirelessly without involving control system 33 in the communication path in the FIG. 6E example.

Figure 6F:
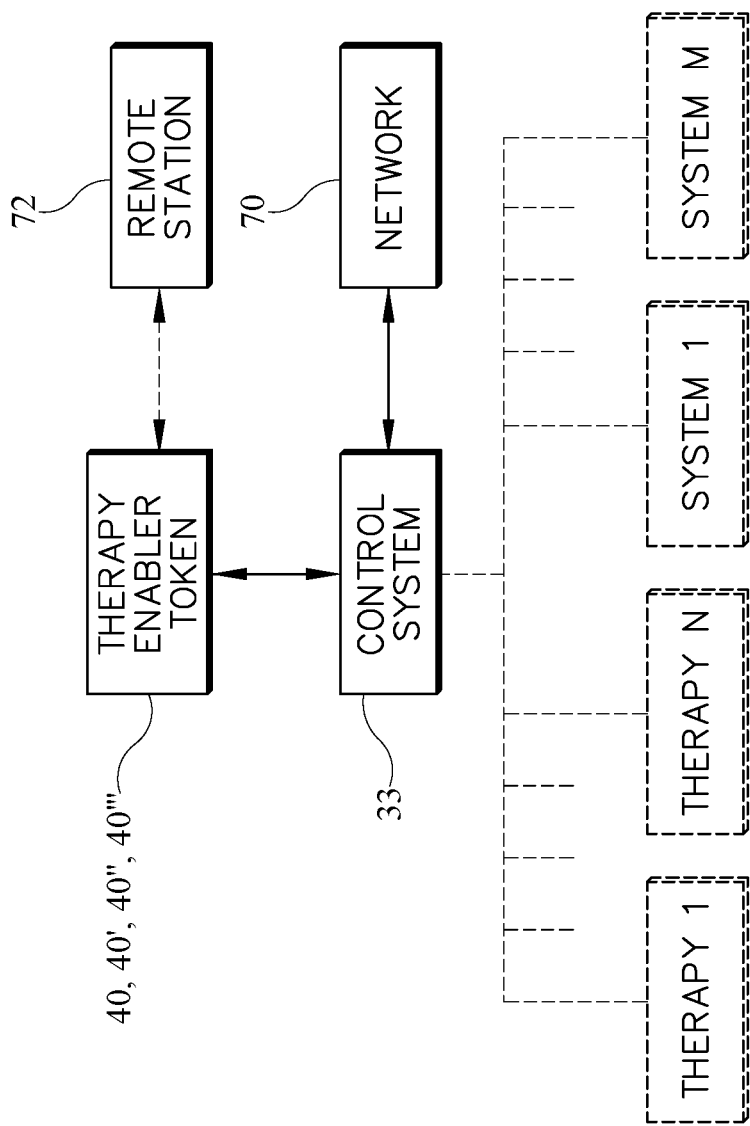
FIG. 6F is a block diagram, similar to FIG. 6D, but having the controller also in communication with a network of a healthcare facility.

In some embodiments having token 40, 40', 40", 40'" communicating wirelessly with remote station 72, control system 33 is also in communication with network 70 as shown diagrammatically in FIG. 6F. Other than the addition of network 70 in communication with control system 33, FIG. 6F is the same as FIG. 6E. Thus, the discussion above with regard to FIG. 6E is equally applicable to FIG. 6F.

According to this disclosure, each of tokens 40, 40', 40", 40'" may be thought of, or referred to, as an annunciator which in some respect announces its presence and transmits information to reader 38, which may be thought of, or referred to, as a discriminator which passes the information onto control system 32, 33. In some embodiments, the information on tokens 40, 40', 40", 40'" is reprogrammable via a program interface, such as a wireless interface, wired interface, or a direct connection, with a device, such as a computer, that is configured to reprogram one or more of tokens 40, 40', 40", 40'". Thus, in some embodiments, tokens 40, 40', 40", 40'" are reprogrammed when coupled to the patient support structure. In other embodiments, tokens 40, 40', 40", 40'" are reprogrammed when separated from the patient support structure, such as being reprogrammed with wireless signals.

In some embodiments, the software or code on token 40, 40', 40", 40'" is transferred to memory, such as random access memory (RAM) of the control system 32, 33 for continued storage therein even after token 40, 40', 40", 40'" is decoupled electronically from system 32, 33. However, it is contemplated by this disclosure that, even though the software code for operating one or more therapies of surface 12 is left behind in the memory of system 32 and/or system 33, an appropriate token 40, 40', 40", 40'" still needs to be electronically coupled to system 32, 33 before the one or more therapies are enabled. In some embodiments, the absence of token 40, 40' 40", 40'" breaks a circuit that results in depowering the RAM of system 32, 33. As alluded to above, it is also contemplated by this disclosure that one or more parameters or permission codes are read by system 32 and/or system 33 from certain memory addresses of token 40, 40', 40", 40'".

It is within the scope of this disclosure for token 40, 40', 40", 40'" to be in communication, either wired or wireless as the case may be, with a remote computer that, in turn, communicates via a network, such as an Ethernet, with bed 10 to enable the therapy function(s) of bed 10. Thus, token 40, 40', 40", 40'" may be in relatively close proximity to and in communication with a central station, such as a master nurse call station, for example, and enable the therapy function(s) of one or more beds 10 remotely. According to such an alternative embodiment, a single one of tokens 40, 40', 40", 40'" may be designated for enabling a predetermined number of beds (e.g., one or more) and then the caregiver at the central station can designate which beds in a nursing unit or wing, for example, are the one or more beds that have their therapies enabled by the token 40, 40', 40", 40'". The appropriate enablement or permission code is then transmitted from the central station to the designated one or more beds to enable the therapy or therapies.

Although certain illustrative embodiments have been described in detail above, many embodiments, variations and modifications are possible that are still within the scope and spirit of this disclosure as described herein and as defined in the following claims.

The invention claimed is:

1. A therapy enabler apparatus for use with a patient support apparatus, the therapy enabler apparatus comprising a therapy enabler token having a memory containing first data that is transferrable to a reader of the patient support apparatus to enable a first therapy of the patient support apparatus, the memory being reprogrammable by a remote computer over a network with second data that is transferrable to the reader of the patient support apparatus to enable a second therapy of the patient support apparatus, the memory of the therapy enabler token being reprogrammable while the therapy enabler token is in communication with the reader of the patient support apparatus.

2. The therapy enabler apparatus of claim 1, wherein the therapy enabler token includes a transmitter or transceiver to provide wireless communication between the memory of the therapy enabler token and the reader of the patient support apparatus.

3. The therapy enabler apparatus of claim 1, wherein the memory of the therapy enabler token is reprogrammed via communication from the network, through control circuitry of the patient support apparatus, and through the reader of the patient support apparatus.

4. The therapy enabler apparatus of claim 1, wherein the memory of the therapy enabler token is reprogrammed via wireless communication from control circuitry of the patient support apparatus which is in communication with the network.

5. The therapy enabler apparatus of claim 1, wherein the memory of the therapy enabler token is reprogrammed via communication from the network without involving any control circuitry of the patient support apparatus.

6. The therapy enabler apparatus of claim 1, wherein the therapy enabler token also enables bed frame movements of the patient support apparatus that are otherwise locked out from use.

7. The therapy enabler apparatus of claim 6, wherein bed frame movements include movement of a bed frame of the patient support apparatus to a chair egress position.

8. The therapy enabler apparatus of claim 1, wherein a software update for the patient support apparatus is stored in the memory of the therapy enabler token and is uploaded to control circuitry of the patient support apparatus from the therapy enabler token via the reader.

9. The therapy enabler apparatus of claim 8, wherein the software update is transmitted to the therapy enabler token by a remote computer in response to being signaled by control circuitry of the patient support apparatus that the therapy enabler token is communicating with the reader.

10. The therapy enabler apparatus of claim 1, wherein an operational parameter for the patient support apparatus is stored in the memory of the therapy enabler token and is transmitted to control circuitry of the patient support apparatus from the therapy enabler token via the reader.

11. The therapy enabler apparatus of claim 1, wherein the memory of the therapy enabler token is reprogrammable via a wired interface.

12. The therapy enabler apparatus of claim 11, wherein the memory of therapy enabler token is reprogrammed when the therapy enabler token is physically connected to the patient support apparatus.

13. The therapy enabler apparatus of claim 12, wherein a physical connection to the patient support apparatus is made via insertion of the therapy enabler token into an opening in a footboard of the patient support apparatus.

14. The therapy enabler apparatus of claim 12, wherein a physical connection to the patient support apparatus is made via insertion of the therapy enabler token into an opening in a siderail of the patient support apparatus.

15. The therapy enabler apparatus of claim 12, wherein a physical connection to the patient support apparatus is made via insertion of the therapy enabler token into an opening in a mattress of the patient support apparatus.

16. The therapy enabler apparatus of claim 1, wherein the therapy enabler token is configured to be worn by a patient.

17. The therapy enabler apparatus of claim 16, wherein the therapy enabler token is included as part of a wristband to be worn on a patient's wrist.

18. The therapy enabler apparatus of claim 1, wherein the memory of the therapy enabler token is reprogrammed wirelessly when the therapy enabler token is separated from the patient support apparatus.

19. The therapy enabler apparatus of claim 1, wherein the memory comprises one or more of the following: an RFID circuit, a serial data transfer circuit, a resistor network, a ROM chip, an EPROM chip, or an EEPROM chip.

20. The therapy enabler apparatus of claim 1, wherein the patient support apparatus includes an air mattress, the first therapy comprises controlling inflation of the air mattress in a first manner, and the second therapy comprises controlling inflation of the air mattress in a second manner.

21. The therapy enabler apparatus of claim 1, wherein the first therapy comprises compression therapy.

22. The therapy enabler apparatus of claim 21, wherein the compression therapy is applied by at least one air bladder that is configured as a compression therapy garment.

23. The therapy enabler apparatus of claim 22, wherein the compression therapy garment comprises a wrap, a sleeve, or a boot, that is worn on a patient's limb.

24. The therapy enabler apparatus of claim 1, wherein the first therapy comprises sequential compression therapy.

25. The therapy enabler apparatus of claim 24, wherein the sequential compression therapy is applied by at least one air bladder that is configured as a sequential compression therapy garment.

26. The therapy enabler apparatus of claim 25, wherein the sequential compression therapy garment comprises a wrap, a sleeve, or a boot, that is worn on a patient's limb.

27. A patient support apparatus comprising a patient support structure having a surface configured to support a patient in a recumbent position, the patient support structure being configured to provide compression therapy to a limb of a patient by operation of compression therapy components that are carried on the patient support structure, and a therapy enabler token, the compression therapy being disabled when the therapy enabler token is communicatively decoupled from the patient support structure, and the compression therapy being enabled in response to the therapy enabler token being communicatively coupled with the patient support structure.

28. The patient support apparatus of claim 27, wherein the compression therapy is applied by at least one air bladder that is configured as a compression therapy garment.

29. The patient support apparatus of claim 28, wherein the compression therapy garment comprises a wrap, a sleeve, or a boot.

30. The patient support apparatus of claim 27, wherein the compression therapy comprises sequential compression therapy.

31. The patient support apparatus of claim 30, wherein the sequential compression therapy is applied by at least one air bladder that is configured as a sequential compression therapy garment.

32. The patient support apparatus of claim 31, wherein the sequential compression therapy garment comprises a wrap, a sleeve, or a boot.

33. The patient support apparatus of claim 27, wherein the surface includes a mattress having at least one inflatable bladder that is operable to deliver a mattress therapy to the patient, the mattress therapy being disabled when the therapy enabler token is communicatively decoupled from the patient support structure, and the mattress therapy being enabled in response to the therapy enabler token being communicatively coupled with the patient support structure.

* * * * *